United States Patent [19]

Fisher et al.

[11] 4,410,755

[45] Oct. 18, 1983

[54] METHOD TO PURIFY ALPHA-METHYL STYRENE PRIOR TO CATALYTIC HYDROGENATION

[75] Inventors: William B. Fisher; Jan F. Van Peppen, both of Chester, Va.

[73] Assignee: Allied Corporation, Morris Township, Morris County, N.J.

[21] Appl. No.: 385,238

[22] Filed: Jun. 4, 1982

Related U.S. Application Data

[63] Continuation-in-part of Ser. No. 208,903, Nov. 11, 1980, Pat. No. 4,334,107.

[51] Int. Cl.$^3$ .............................................. C07C 7/00
[52] U.S. Cl. .................................... 585/800; 568/749
[58] Field of Search ................ 568/754, 749; 585/850, 585/800

[56] References Cited

U.S. PATENT DOCUMENTS

| | | | |
|---|---|---|---|
| 2,992,169 | 7/1961 | Gregory et al. | 568/754 |
| 3,076,810 | 2/1963 | Doggen et al. | 568/835 |
| 3,290,384 | 12/1966 | Largmar et al. | 568/568 |
| 3,305,586 | 2/1967 | Phielix | 568/376 |
| 3,646,235 | 2/1972 | Little et al. | 585/754 |
| 3,692,845 | 9/1972 | Cheema et al. | 568/754 |
| 4,334,107 | 6/1982 | Peppen | 568/749 |

*Primary Examiner*—Werren B. Lone
*Attorney, Agent, or Firm*—Richard A. Anderson

[57] ABSTRACT

Alpha-methyl styrene, obtained as a byproduct in the manufacture of phenol is hydrogenated to cumene using hydrogen and standard hydrogenation catalysts which are selective for the ethylenic side chain. Prior to hydrogenation the alpha-methyl styrene is treated to effect removal of hydroxy acetone present. By reducing or eliminating hydroxy acetone, poisoning of the catalyst is prevented. Hydroxy acetone is removed from the alpha-methyl styrene by catalytic pretreatment.

7 Claims, No Drawings

METHOD TO PURIFY ALPHA-METHYL STYRENE PRIOR TO CATALYTIC HYDROGENATION

BACKGROUND OF THE INVENTION

This application is a continuation-in-part of Ser. No. 208,903 filed Nov. 11, 1980, now U.S. Pat. No. 4,334,107 by J. F. VanPeppen to issue June 8, 1982.

A portion of the background of this invention is fully set forth in U.S. Pat. No. 3,646,235, hereby incorporated by reference, in toto.

This invention also relates to the purification of phenol produced by the oxidation of cumene, more specifically, the removal of acetol and alpha-methyl styrene from crude phenol by reaction in the presence of a catalyst, to purify for the subsequent hydrogenation of phenol process.

Production of phenol by oxidation of cumene is known, such as in U.S. Pat. No. 3,290,384 hereby incorporated by reference. The subsequent hydrogenation of phenol to cyclohexanone is known, such as in U.S. Pat. No. 3,076,810, or for the vapor phase process, U.S. Pat. No. 3,305,586, both hereby incorporated by reference. Various processes for purification of phenol prior to hydrogenation are also known, such as in U.S. Pat. No. 3,965,187; U.S. Pat. No. 2,992,169 and U.S. Pat. No. 3,692,845, all hereby incorporated by reference.

Phenol produced by the cumeme oxidation process contains constituents which lower the rate of hydrogenation relative to a purified phenol. Additionally, these constituents generate carbon monoxide. Carbon monoxide is known to deactivate the catalyst used in the phenol hydrogenation process (palladium on carbon or other support). When the phenol produced from cumene was pretreated with di- and polyfunctional aliphatic, alicyclic or aromatic amines and then distilled, the harmful constituents were apparently removed as the rate of hydrogenation was relatively high and only very small amounts of carbon monoxide were generated during the hydrogenation reaction.

SUMMARY OF THE INVENTION

We have now found that when the phenol produced from cumene was heated to 180° C. in the presence of palladium on carbon catalyst, while nitrogen was purged through the reaction mixture, carbon monoxide was generated. When the carbon monoxide generated had subsided and the nitrogen purge was replaced by hydrogen, the rate of hydrogenation at 160° C. was as fast as that of phenol pretreated with the di- and polyfunctional amines followed by distillation. Also when acetol was added to phenol pretreated with di- and polyfunctional amines the generation of carbon monoxide was very high.

It has been observed that acetol and alpha-methyl styrene, both constituents in phenol produced from cumene, can react to form cumene and pyruvic aldehyde. The latter may decompose into carbon monoxide and acetaldehyde as shown in the following reaction equation:

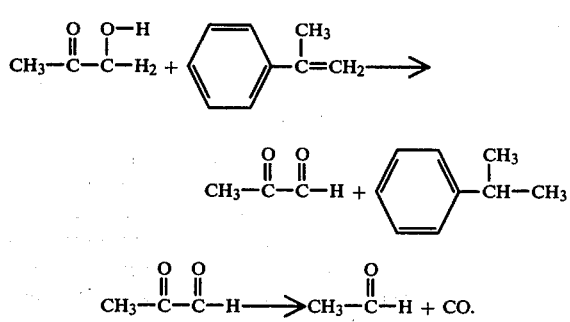

The reaction of acetol with alpha-methyl styrene to form cumene does not proceed without catalyst. Palladium on carbon was found to be effective; nickel (supported and Raney-type) was not. The reaction involves the transfer of one mole of hydrogen from acetol to alpha-methyl styrene. The dehydrogenation product from acetol, presumably pyruvic aldehyde

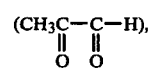

was not stable under reaction conditions. Other noble metal catalysts or palladium on other supports capable of catalyzing the hydrogen transfer reaction between acetol and alpha-methyl styrene may also be used in the invention. Other supports are aluminum oxide or silica, and other noble metals are platinum, rhodium or ruthenium. The reaction can be carried out at 160° C. The acetol and alpha-methyl styrene are byproducts in the cumene oxidation process in phenol. They are believed to be formed as shown in the following scheme:

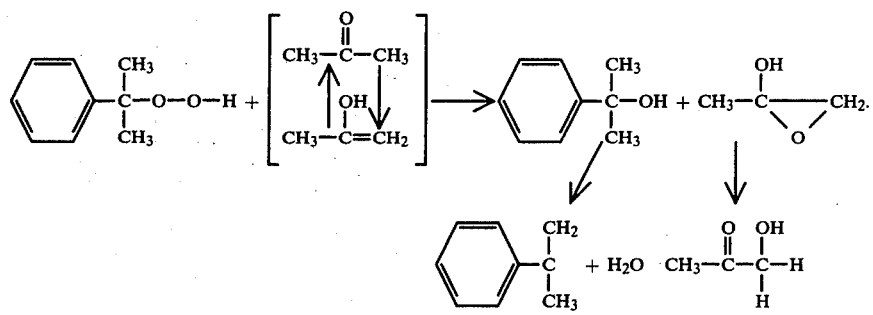

On the assumption that acetol and alpha-methyl styrene are formed by the above scheme only, the molar ratio of these two should, therefore, be 1:1. Both compounds are nuisance byproducts. Acetol poisons the catalyst in the phenol hydrogenation and alpha-methyl styrene is difficult to remove in the phenol rectification and from the cumene recycled in the process. Taking advantage of the discovered reaction of this invention, the removal of these byproducts can be facilitated.

Specifically, the invention is a method to purify crude phenol containing acetol and alpha-methyl styrene prior to hydrogenation comprising contacting the crude phenol with catalyst while heating the crude phenol and catalyst to a temperature between about 140° C. and about 190° C., more specifically between 160° C. and 183° C.

at a pressure between about atmospheric and about 70 psig in an inert atmosphere so that the catalyst causes a reaction between the impurities acetol and alpha-methyl styrene to form cumene and pyruvic aldehyde, then heating the resultant compounds at a pressure between atmospheric and about 70 psig for a period of 0.1 to about six hours, more preferably for a period of 2 to 4 hours, under an inert gas sweep to a temperature of from about 150° C. to about 190° C., more preferably between 160° C. and 183° C., until the pyruvic aldehyde has decomposed and its decomposition products are swept away in the gas sweep.

The catalyst effective in the reaction between acetol and alpha-methyl styrene is palladium on carbon or any other catalyst capable of catalyzing the hydrogen transfer between the acetol and alpha-methyl styrene.

In a commercial continuous process, heated crude phenol would be continuously passed across heated catalyst to continuously convert the impurities to pyruvic aldehyde and cumene, while the previously formed pyruvic aldehyde would continuously decompose and be continuously removed with an inert nitrogen sweep.

The method of this invention can also be used to purify crude alpha-methyl styrene containing acetol prior to hydrogenation by contacting the crude alpha-methyl styrene with a catalyst while heating the crude alpha-methyl styrene and catalyst to a temperature between about 24° C. and about 400° C. at a pressure between about atmospheric and about 1000 psig in an inert atmosphere. The catalyst causes a reaction between the impurity acetol and alpha-methyl styrene to form cumene and pyruvic aldehyde. Then, by heating the resultant compounds for a period of 0.1 to about six hours under an inert gas sweep to a temperature of about 24° C. to about 400° C., the pyruvic aldehyde decomposes and its decomposition products are swept away in a gas sweep. It is preferred that the catalyst be selected from the group consisting of palladium, platinum, rhodium and ruthenium supported on a support selected from the group consisting of carbon, aluminum oxide and silica. Most preferred is palladium on carbon support. The preferred temperature to heat the crude alpha-methyl styrene and catalyst is between about 120° C. and 180° C. and likewise the resultant compound should be heated to a temperature of between about 120° C. and 180° C. at a pressure between about 10 and 100 psig. The preferred method of purifying the crude alpha-methyl styrene should be carried out for a period of about 2 to 4 hours and likewise the resultant compounds are heated for a period of about 2 to 4 hours. Even more preferred is to carry out the continuous process wherein the heating steps are carried out at a temperature of from about 120° C. to about 180° C. for a period of about 2 to 4 hours, and most preferably the heating steps are carried out simultaneously.

DESCRIPTION OF THE PREFERRED EMBODIMENT

Charged to an autoclave were 9,000 parts of phenol, 500 parts of alpha-methyl styrene, 500 parts of acetol and 32 parts of 5 percent palladium on carbon catalyst. The mixture was heated to 160° C. under 54 psig nitrogen pressure while agitated. Samples were withdrawn after 0.5 hour, 2 hours and 4 hours. Analysis by gas phase chromatography showed the disappearance of alpha-methyl styrene and acetol and the formation of cumene. These results are confirmed by mass spectrometry. The conversions appeared to be complete after four hours.

We have found that one of the major factors contributing to the poisoning of catalyst systems when alpha-methyl styrene is hydrogenated, is the presence of a carbonyl compound formed along with alpha-methyl styrene during the manufacture of phenol from cumene. This carbonyl compound is known as 1-hydroxy-2-propanone, hydroxy acetone or acetol. More specifically, we have found that when hydroxy acetone is present along with alpha-methyl styrene, the effectiveness of a hydrogenation catalyst is greatly reduced. Accordingly, the present invention relates to an improved process for hydrogenating alpha-methyl styrene, obtained as a byproduct during the decomposition of cumene hydroperoxide, using hydrogen and a hydrogenation catalyst wherein the alpha-methyl styrene is essentially free of hydroxy acetone.

As has been previously stated, when cumene hydroperoxide is decomposed with an acid catayst, the mixture thus obtained contains among the identifiable products, phenol, dimethylphenyl carbinol, acetophenone, alpha-methyl styrene, para-alpha-cumylphenol and water. These byproducts are separated and removed in separate streams by fractional distillation. Analysis of the crude alpha-methyl styrene so obtained (Table 1) indicates that a number of identifiable products are carried over with alpha-methyl styrene and further investigation has revealed that although these impurities do somewhat inhibit the hydrogenation, that hydroxy acetone severely poisons a hydrogenation catalyst.

TABLE 1

Contents of Typical Sample of Crude Alpha-Methyl Styrene Obtained as a Byproduct in the Manufacture of Phenol

|  | Percent |
|---|---|
| alpha-methyl styrene | 74.0 |
| acetone | 0.2 |
| hydroxyacetone | 1.3 |
| acetophenone | 0.2 |
| 2,2-dimethylphenyl carbinol | 1.8 |
| phenol | 21.1 |
| alpha-methyl styrene dimers | 1.1 |
| water | 0.6 |
| unknowns | 0.3 |

Hydrogenation of other streams containing alpha-methyl styrene and acetol has confirmed that catalyst life and/or rate of hydrogenation is directly related to the amount of hydroxyacetone present. Where concentrations are small (i.e., less than 0.1 weight percent), as for example in acetone column bottoms, catalyst life is longer than in alpha-methyl styrene obtained from the overhead of the acetone columns where hydroxyacetone concentrate is as high as 1%.

The method of removal of acetol (also known as hydroxyacetone) is by contacting the crude alpha-methyl styrene with catalyst while heating to a temperature of between about 24° C. and about 400° C. The catalyst causes a reaction between the acetol and the alpha-methyl styrene to form cumene and pyruvic aldehyde. By heating the cumene and pyruvic aldehyde for about an hour at 24° C. to 400° C. the pyruvic aldehyde is decomposed and can be carried away in a gas sweep. The cumene can be recovered such as by distillation and recycled to be combined with virgin cumene as feed. The catalyst used to remove acetol can be the same or different than the catalyst used to hydrogenate alpha-methyl styrene, as described below. In a commercial process, heated crude alpha-methyl styrene would be continuously passed across heated purification catalyst to continuously convert the acetol impurity to pyruvic aldehyde and cumene, while using an inert sweep such as nitrogen to sweep away the decomposition products of pyruvic aldehyde.

EXAMPLE

Alpha-methyl styrene, 9,500 parts, 500 parts of acetol and 32 parts of 5 percent on palladium on carbon catalyst are charged to an autoclave, being agitated and heated to 160° C. under 54 psig nitrogen pressure, for four hours and mass spectrometry analysis by gas phase chromatography would show disappearance of acetol, substantially all the same small portions of alpha-methyl styrene and formation of cumene. The purified alpha-methyl styrene is now ready for hydrogenation.

In hydrogenating alpha-methyl styrene according to the present invention the particular steps are also not critical. As has been previously stated, the prior art adequately teaches many methods for hydrogenating alpha-methyl styrene under varying reaction conditions and employing numerous catalyst systems and all of these are employable in the present invention. For example, the prior art indicates that alpha-methyl styrene can be catalytically hydrogenated in the liquid or vapor phase at temperatures ranging from 24° C. to 400° C. and at pressures ranging from 0 to 5000 psig. Similarly, a variety of catalysts and catalyst supporting systems have been satisfactorily employed. Exemplary of a few of these catalysts include platinum metals, especially palladium, cobalt, and chromium oxide and catalysts comprising mixtures of nickel, chromium and copper as described in German Pat. No. 1 134 361. The aforementioned catalysts have been employed in amounts ranging from 0.5 to 10 percent by weight, suspended in a liquid or supported on external surfaces (pellet or powder) of aluminum oxide, silica acid, diatomaceous earth, charcoal, or Filter Gel, and are present in only minor or catalytic amounts when considering the total catalyst charge in relationship to the total reaction mixture.

Although as previously stated the particular catalyst and reaction conditions are not critical to the invention, it must be appreciated that certain catalysts are less expensive and more active and selective for hydrogenating the ethylenic side chain of alpha-methyl styrene, rather than the aromatic nucleus than others, and it is expected that the choice of a particular catalyst will be governed accordingly. It is preferred to use palladium or platinum, but preferably palladium on carbon, with palladium in amounts ranging from 1 to 5 percent. It is preferred to effect the hydrogenation of alpha-methyl styrene under conditions wherein the temperature is maintained at about 24° C. to 120° C. and at a pressure of 10 to 100 psig, and preferably at about 24° C. to 50° C. and 10 to 50 psig.

We claim:

1. A method to purify crude alpha-methyl styrene containing acetol prior to hydrogenation comprising
    contacting the crude alpha-methyl styrene with a catalyst while
    heating the crude alpha-methyl styrene and catalyst to a temperature between about 24° C. and about 400° C.
    at a pressure between about atmospheric and about 1000 psig
    in an inert atmosphere
    so that the catalyst causes a reaction between the impurity acetol and alpha-methyl styrene to form cumene and pyruvic aldehyde, then
    heating the resultant compounds for a period of 0.1 to about six hours under an inert gas sweep to a temperature of from about 24° C. to about 400° C. until the pyruvic aldehyde decomposes and its decomposition products are swept away in the gas sweep.

2. The method of claim 1 wherein the catalyst is selected from the group consisting of palladium, platinum, rhodium and ruthenium supported on a support selected from the group selected from the group consisting of carbon, aluminum oxide and silica.

3. The method of claim 2 wherein the catalyst is palladium on a carbon support.

4. The method of claim 1 wherein the crude alpha-methyl styrene and the catalyst are heated to a temperature between about 120° C. and 180° C. and likewise the resultant compounds are heated to a temperature between about 120° C. to 180° C. at a pressure between about 10 and about 100 psig.

5. The method of claim 1 wherein the heating of the crude alpha-methyl styrene and the catalyst is carried out for a period of from about 2 to about 4 hours, and likewise the resultant compounds are heated for a period of from about 2 to about 4 hours.

6. The method of claim 3 wherein the process is continuous and both heating steps are carried out at a temperature of from about 120° C. to 180° C. for a period of about 2 to about 4 hours.

7. The continuous process of claim 6 wherein both heating steps are carried out simultaneously.

* * * * *